United States Patent
Ito et al.

(10) Patent No.: US 11,638,686 B2
(45) Date of Patent: May 2, 2023

(54) COSMETIC PREPARATION

(71) Applicant: Shiseido Company, Ltd., Tokyo (JP)

(72) Inventors: Ryoya Ito, Tokyo (JP); Kouichi Nagai, Tokyo (JP); Kei Ujimoto, Tokyo (JP); Yuko Nagare, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 48 days.

(21) Appl. No.: 17/267,328

(22) PCT Filed: Aug. 9, 2019

(86) PCT No.: PCT/JP2019/031598
§ 371 (c)(1),
(2) Date: Feb. 9, 2021

(87) PCT Pub. No.: WO2020/032244
PCT Pub. Date: Feb. 13, 2020

(65) Prior Publication Data
US 2021/0228471 A1 Jul. 29, 2021

(30) Foreign Application Priority Data
Aug. 10, 2018 (JP) .............................. JP2018-151680

(51) Int. Cl.
| | |
|---|---|
| *A61K 8/86* | (2006.01) |
| *A61K 8/25* | (2006.01) |
| *A61K 8/27* | (2006.01) |
| *A61K 8/29* | (2006.01) |
| *A61K 8/31* | (2006.01) |
| *A61K 8/37* | (2006.01) |
| *A61K 8/60* | (2006.01) |
| *A61K 8/73* | (2006.01) |
| *A61Q 17/04* | (2006.01) |

(52) U.S. Cl.
CPC ............... *A61K 8/86* (2013.01); *A61K 8/25* (2013.01); *A61K 8/27* (2013.01); *A61K 8/29* (2013.01); *A61K 8/31* (2013.01); *A61K 8/37* (2013.01); *A61K 8/602* (2013.01); *A61K 8/732* (2013.01); *A61Q 17/04* (2013.01)

(58) Field of Classification Search
None
See application file for complete search history.

(56) References Cited

U.S. PATENT DOCUMENTS

2010/0209365 A1\* 8/2010 Takakura ............... A61K 8/375
424/59
2018/0289610 A1 10/2018 Yamaki et al.

FOREIGN PATENT DOCUMENTS

| EP | 3 213 741 A1 | 9/2017 |
| JP | 2009-024012 A | 2/2009 |
| JP | 2012-012351 A | 1/2012 |
| WO | WO-2016/068300 A1 | 5/2016 |
| WO | WO-2016/138249 A1 | 9/2016 |
| WO | WO-2017/057676 A1 | 4/2017 |

OTHER PUBLICATIONS

Database GNPD [Online] MINTEL, "Cream SPF 50+," Shiseido, Sep. 8, 2015, Database accession No. 3281253, XP055903717, 4 pages.
Database GNPD [Online] MINTEL, "UV Protective Cream SPF 50+ PA++++," Shiseido, Jun. 13, 2018, Database accession No. 5749529, XP055903725, 3 pages.
Database GNPD [Online] MINTEL, "Whitening Essence Facial UV Sunscreen SPF 40+/PA++++," Shiseido, Jun. 27, 2016, Database accession No. 4100943, XP055903724, 3 pages.

\* cited by examiner

*Primary Examiner* — Nannette Holloman
(74) *Attorney, Agent, or Firm* — Foley & Lardner LLP

(57) ABSTRACT

The present invention relates to a cosmetic having the innovative, unprecedented property in which the ultraviolet protection effects do not decrease, but conversely increase, due to coming into contact with moisture such as water or perspiration, and due to heat applied in the usage environment. The cosmetic of the present invention contains
(A) an ultraviolet protectant;
(B) at least one compound that is water-soluble and that has an IOB of 5.0 or lower, selected from among (i) alkylene oxide derivatives and (ii) polyhydric alcohols; and
(C) an oil phase thickener;
wherein
the mass ratio of component (A)/component (B) is 20 or lower; and
the (B) (i) alkylene oxide derivatives are polyoxyalkylene/polyoxyethylene copolymer dialkyl ethers represented by the following formula (I):

$$R_1O\text{---}[(AO)_m(EO)_n]\text{---}R_2 \qquad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, $1 \leq m \leq 70$, $1 \leq n \leq 70$ and $m+n \leq 40$.

3 Claims, No Drawings

COSMETIC PREPARATION

CROSS-REFERENCE TO RELATED APPLICATIONS

This application is the U.S. National Stage of PCT/JP2019/031598, filed Aug. 9, 2019, which claims priority to JP 2018-151680, filed Aug. 10, 2018.

TECHNICAL FIELD

The present invention relates to a cosmetic having sunscreen effects. More specifically, the present invention relates to a cosmetic having both excellent water resistance and heat resistance, and having the unprecedented properties in which heating and contact with moisture such as water or perspiration increases the ultraviolet protection effects over those immediately after applying the cosmetic.

BACKGROUND ART

Protecting the skin from harm due to ultraviolet rays is an important problem in skin care and body care, and various types of UV-care cosmetics have been developed in order to minimize the detrimental impact that ultraviolet rays have on skin. Sunscreen cosmetics, which are one type of UV-care cosmetic, protect the skin from harm due to ultraviolet rays by containing ultraviolet absorbing agents and ultraviolet scattering agents, thereby blocking UVA and UVB from reaching the skin (Non-Patent Document 1). Recently, it has come to be considered important to protect the skin from ultraviolet rays in daily life, and not only under harsh ultraviolet conditions during outdoor activities such as bathing in pools or in the ocean in summertime or skiing in wintertime. Thus, even among normal skin-care cosmetic products, those having ultraviolet protection effects are sought.

The ultraviolet protection effects due to sunscreen products are obtained by the ultraviolet protectants, i.e., by the ultraviolet absorbing agents or ultraviolet scattering agents that are added. However, ultraviolet absorbing agents include some in which the ultraviolet absorption performance decreases due to irradiation by light (photodegradation). Additionally, ultraviolet absorbing agents and ultraviolet scattering agents can flow away from the skin surface upon coming into contact with moisture.

Many improvements have been proposed for suppressing the photodegradation of ultraviolet protection effects (Patent Document 1), and regarding water resistance, a cosmetic having the innovative property in which contact with moisture does not decrease the ultraviolet protection effects but conversely increases the protection effects has been developed (Patent Document 2).

Meanwhile, as with light and moisture, decreases in ultraviolet protection effects due to heat cannot be ignored. In general, when a cosmetic that has been applied to skin is heated, the ultraviolet absorbing agents and other components contained in the cosmetic are degraded, thereby decreasing the ultraviolet protection effects. However, regarding heat, although there are examples in which the impact of heat, for example, on the emulsion stability of emulsion cosmetics including cosmetics have been considered (Patent Document 3), changes in the ultraviolet protection effects due to heat have not been considered until now, and cosmetics having the purpose of suppressing decreases in ultraviolet protection effects due to heat have not previously been proposed.

RELATED ART

Patent Documents

Patent Document 1: JP 2010-150172 A
Patent Document 2: WO 2016/068300
Patent Document 3: JP 4397286 B Non-Patent Documents Non-Patent Document 1: Shin-keshohin-gaku [New Cosmetology], 2nd edition, edited by Takeo Mitsui, 2001, published by Nanzando, pp. 497-504

SUMMARY OF THE INVENTION

Problem to be Solved by the Invention

An objective of the present invention, in a research process for developing a cosmetic having strong ultraviolet protection effects, is to provide a cosmetic having the innovative, unprecedented property in which the ultraviolet protection effects do not decrease, but conversely increase, due to coming into contact with moisture such as water or perspiration, and due to heat applied in the usage environment.

Means for Solving the Problem

As a result of performing diligent research towards solving the above-mentioned problem, the present inventors discovered that a cosmetic having the aforementioned novel properties that is the objective can be obtained by blending, at a prescribed proportion, an ultraviolet protectant, a specific alkylene oxide or polyhydric alcohol, and a specific oil phase thickener, thereby completing the present invention.

In other words, the present invention mainly provides a cosmetic containing
  (A) an ultraviolet protectant;
  (B) at least one compound that is water-soluble and that has an IOB of 5.0 or lower, selected from among (i) alkylene oxide derivatives and (ii) polyhydric alcohols; and
  (C) an oil phase thickener;
wherein
  the mass ratio of component (A)/component (B) is 20 or lower; and
  the (B) (i) alkylene oxide derivatives are polyoxyalkylene/polyoxyethylene copolymer dialkyl ethers represented by the following formula (I):

$$R_1O\text{—}[(AO)_m(EO)_n]\text{—}R_2 \quad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, $1 \leq m \leq 70$, $1 \leq n \leq 70$ and $m+n \leq 40$.

Effects of the Invention

With the cosmetic of the present invention, the ultraviolet protection effects significantly increase after coming into contact with water, perspiration and the like, and after being heated during actual use, in comparison to those immediately after the cosmetic has been applied to the skin. In other words, the cosmetic according to the present invention is an innovative cosmetic having the property, contrary to conventional expectations, in which moisture and heat, which had been considered to cause degradation of the effects in conventional cosmetics, conversely increase the ultraviolet protection effects.

MODES FOR CARRYING OUT THE INVENTION

Hereinafter, the present invention will be explained in detail.

The cosmetic of the present invention essentially contains (A) an ultraviolet protectant, (B) a prescribed alkylene oxide derivative or polyhydric alcohol, and (C) an oil phase thickener. Hereinafter, the respective components constituting the cosmetic of the present invention will be explained in detail.

<(A) Ultraviolet Protectant (Ultraviolet Absorbing Agent and/or Ultraviolet Scattering Agent)>

The (A) ultraviolet protectant (hereinafter sometimes referred to simply as "component (A)") blended into the cosmetic according to the present invention refers to an ultraviolet absorbing agent and/or an ultraviolet scattering agent, and any type that is normally blended into cosmetics may be used.

The ultraviolet absorbing agents that can be used in the present invention are not particularly limited, but examples include benzoic acid derivatives, salicylic acid derivatives, cinnamic acid derivatives, dibenzoyl methane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g. "Escalol 507"; ISP), glyceryl PABA, PEG-25-PABA (e.g. "Uvinul P25"; BASF), diethylamino hydroxybenzoyl hexyl benzoate (e.g. "Uvinul A Plus") and the like.

Examples of salicylic acid derivatives include homosalate ("Eusolex HMS"; Rona/EM Industries), ethylhexyl salicylate or octyl salicylate (e.g. "Neo Heliopan OS"; Haarmann & Reimer), dipropylene glycol salicylate (e.g. "Dipsal"; Scher), TEA salicylate (e.g. "Neo Heliopan TS"; Haarmann & Reimer) and the like.

Examples of cinnamic acid derivatives include octyl methoxycinnamate or ethylhexyl methoxycinnamate (e.g. "Parsol MCX"; DSM), isopropyl methoxycinnamate, isoamyl methoxycinnamate (e.g. "Neo Heliopan E1000"; Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g. "Parsol 1789"; DSM) and the like.

Examples of β,β-diphenyl acrylate derivatives include octocrylene (e.g. "Uvinul N539T"; BASF) and the like.

Examples of benzophenone derivatives include benzophenone-1 (e.g. "Uvinul 400"; BASF), benzophenone-2 (e.g. "Uvinul D50"; BASF), benzophenone-3 or oxybenzone (e.g. "Uvinul M40"; BASF), benzophenone-4 (e.g. "Uvinul MS40"; BASF), benzophenone-5, benzophenone-6 (e.g. "Helisorb 11"; Norquay), benzophenone-8 (e.g. "SpectraSorb UV-24"; American Cyanamid), benzophenone-9 (e.g. "Uvinul DS-49"; BASF), benzophenone-12 and the like.

Examples of benzylidene camphor derivatives include 3-benzylidene camphor (e.g. "Mexoryl SD"; Chimex), 4-methylbenzylidene camphor, benzylidene camphor sulfonic acid (e.g., "Mexoryl SL"; Chimex), camphor benzalkonium methosulfate (e.g. "Mexoryl SO"; Chimex), terephthalylidene dicamphor sulfonic acid (e.g. "Mexoryl SX"; Chimex), polyacrylamide methylbenzylidene camphor (e.g. "Mexoryl SW"; Chimex) and the like.

Examples of phenylbenzimidazole derivatives include phenylbenzimidazole sulfonic acid (e.g. "Eusolex 232"; Merck), disodium phenyldibenzimidazole tetrasulfonate (e.g. "Neo Heliopan AP"; Haarmann & Reimer) and the like.

Examples of triazine derivatives include bis-ethylhexyloxyphenol methoxyphenyl triazine (e.g. "Tinosorb S"; Ciba Specialty Chemicals), ethylhexyl triazone (e.g. "Uvinul T150"; BASF), diethylhexyl butamido triazone (e.g. "Uvasorb HEB"; Sigma 3V), 2,4,6-tris(diisobutyl-4'-aminobenzalmalonate)-s-triazine, 2,4,6-tris[4-(2-ethylhexyloxycarbonyl)anilino]-1,3,5-triazine and the like.

Examples of phenylbenzotriazole derivatives include drometrizole trisiloxane (e.g. "Silatrizole"; Rhodia Chimie), methylene bis(benzotriazolyl tetramethylbutyl phenol) (e.g. "Tinosorb M" (Ciba Specialty Chemicals)) and the like.

Examples of anthranil derivatives include menthyl anthranilate (e.g. "Neo Heliopan MA"; Haarmann & Reimer) and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups (e.g. Polysilicone-15; "Parsol SLX"; DSM Nutrition Japan) and the like.

Examples of 4,4-diarylbutadiene derivatives include 1,1-dicarboxy (2,2'-dimethylpropyl)-4,4-diphenylbutadiene and the like.

Examples of particularly preferred ultraviolet absorbing agents include, but are not limited to, ethylhexyl methoxycinnamate, octocrylene, dimethicodiethyl benzalmalonate, polysilicone-15, 4-tert-butyl-4'-methoxy dibenzoyl methane (t-butyl methoxy dibenzoyl methane), ethylhexyl triazone, diethylamino hydroxybenzoyl hexyl benzoate, bis-ethylhexyloxyphenol methoxyphenyl triazine, oxybenzone-3, methylene bis-benzotriazolyl tetramethylbutyl phenol, phenylbenzimidazole sulfonic acid, 3-(4'-methylbenzylidene)-d,l-camphor, 3-benzylidene-d,l-camphor, homosalate and ethylhexyl salicylate. In particular, good ultraviolet protection increase effects can be obtained when at least octocrylene is included as component (A).

However, when 4-tert-butyl-4'-methoxy dibenzoyl methane is blended, the blended amount thereof should preferably be small. For example, the amount should preferably be less than 0.5% by mass relative to the total amount of the cosmetic, or 10% by mass or less relative to the total amount of component (A). This is because 4-tert-butyl-4'-methoxy dibenzoyl methane has a tendency to hinder the increase in ultraviolet protection effects due to heating when the (B) alkylene oxide derivative or polyhydric alcohol, and the (C) oil phase thickener are added, thus making it difficult to actually experience a boost in the ultraviolet protection effects due to heat.

The ultraviolet scattering agent used in the present invention is not particularly limited, but specific examples include fine-particle metal oxides such as, for example, zinc oxide, titanium oxide, iron oxide, cerium oxide and tungsten oxide.

The ultraviolet scattering agent may be non-surface-treated or may be treated with various types of hydrophobic surface treatments, but those that are hydrophobically surface-treated are preferably used. As the surface treatment agent, it is possible to use a type that is commonly used in the cosmetics field including, for example, a silicone such as dimethicone and alkyl-modified silicone, an alkoxysilane such as octyltriethoxysilane, a dextrin fatty acid ester such as dextrin palmitate, or a fatty acid such as stearic acid.

The (A) ultraviolet protectant in the present invention includes embodiments consisting only of an ultraviolet absorbing agent, embodiments consisting only of an ultraviolet scattering agent, and embodiments including both an ultraviolet absorbing agent and an ultraviolet scattering agent.

Although the blended amount of the (A) ultraviolet protectant is not particularly limited, the amount should normally be at least 5% by mass, for example, 5% to 40% by mass, preferably 6% to 40% by mass, and more preferably 7% to 30% by mass relative to the total amount of the cosmetic. If the blended amount of the (A) ultraviolet protectant is less than 5% by mass, then sufficient ultraviolet protection effects are difficult to obtain, and even if more than 40% by mass is blended, an increase in the ultraviolet protection effects commensurate with the blended amount cannot be expected, and the stability is worsened.

<(B) Alkylene Oxide Derivative or Polyhydric Alcohol>

The (B) (i) alkylene oxide derivative or (ii) polyhydric alcohol (hereinafter sometimes referred to simply as "component (B)") blended into the cosmetic of the present invention is often blended as a humectant in normal cosmetics. In the present invention, by blending a specific alkylene oxide derivative or polyhydric alcohol, the ultraviolet protection effects, particular after being heated, can be significantly increased in comparison to those immediately after the cosmetic has been applied to skin.

The (B) (i) alkylene oxide derivative or the (ii) polyhydric alcohol must be water-soluble. If a type that is not water-soluble is used, then heating will tend to lower the ultraviolet protection increase effects. In the present invention, "water-soluble" means that at least 0.1% by mass dissolves in water at 25° C.

Additionally, the (B) (i) alkylene oxide derivative or the (ii) polyhydric alcohol has an IOB of 5.0 or lower, more preferably 3.0 or lower, and even more preferably 2.5 or lower. If the IOB value is too high, then there are cases in which ultraviolet protection performance increase effects due to heat cannot be obtained. On the other hand, the lower limit of the IOB value is not particularly limited, but should preferably be at least 0.5, and more preferably at least 0.8.

In this case, IOB is an abbreviation for Inorganic/Organic Balance, which is a value representing the ratio of the inorganic value to the organic value, and which serves as an indicator of the degree of polarity of an organic compound. The IOB value is specifically represented by IOB value=inorganic value/organic value. Regarding the "inorganic value" and the "organic value" respectively, an "inorganic value" and an "organic value" are set for various types of atoms or functional groups so that, for example, the "organic value" is 20 for one carbon atom in a molecule and the "inorganic value" is 100 for one hydroxyl group. By summing the "inorganic values" and the "organic values" of all of the atoms and functional groups in an organic compound, it is possible to compute the IOB value of that organic compound (see, for example, Yoshio Koda, "Yuki Gainenzu—Kiso to Oyo—" [Organic Conceptual Diagram—Fundamentals and Applications], pp. 11-17, Sankyo Shuppan, 1984).

Furthermore, the (B) (i) alkylene oxide derivative or (ii) polyhydric alcohol preferably has an ether bond. By having an ether bond, the component can be considered to more easily dissolve in water than a component not having an ether bond, while also being able to dissolve in oil.

Examples of the (i) alkylene oxide derivative that may be used in the present invention include the polyoxyalkylene/polyoxyethylene copolymer dialkyl ethers represented by the following formula (I):

$$R_1O-[(AO)_m(EO)_n]-R_2 \qquad (I)$$

In the above formula, AO denotes an oxyalkylene group having 3 to 4 carbon atoms. Specific examples include an oxypropylene group, an oxybutylene group, an oxyisobutylene group, an oxytrimethylene group and an oxytetramethylene group, among which an oxypropylene group and an oxybutylene group are preferred. EO represents an oxyethylene group.

$R_1$ and $R_2$, each independently, represent a hydrogen atom or a hydrocarbon group having one to four carbon atoms. Examples of hydrocarbon groups include methyl groups, ethyl groups, n-propyl groups, isopropyl groups, n-butyl groups, sec-butyl groups and tert-butyl groups. Methyl groups and ethyl groups are preferred.

The $R_1$ and $R_2$ in each molecule may be the same type of hydrocarbon group, a mixture of a hydrocarbon group and a hydrogen atom, or a mixture of multiple hydrocarbon groups having different numbers of carbon atoms. However, for each of $R_1$ and $R_2$, the ratio between the numbers of hydrocarbon groups and hydrogen atoms that are present should be such that the ratio (Y/X) of the number (Y) of hydrogen atoms to the number (X) of hydrocarbon groups is preferably 0.15 or lower, and more preferably 0.06 or lower.

The symbol m represents the average number of moles of AO added, such that $1 \leq m \leq 70$, preferably $2 \leq m \leq 20$, and more preferably $2 \leq m \leq 10$. The symbol n represents the average number of moles of EO added, such that $1 \leq n \leq 70$, preferably $2 \leq n \leq 20$, and more preferably $2 \leq n \leq 10$. Additionally, m+n is 40 or less, preferably 25 or less, and more preferably 20 or less. In particular, if m+n is 20 or less, then significantly superior ultraviolet protection increase effects can be obtained by heating.

The order of addition of AO and EO is not particularly limited. AO and EO may be added in the form of blocks so as to form a block copolymer, or may be randomly added so as to form a random copolymer. Block copolymers include not only copolymers with two blocks, but also those having three or more blocks. Preferably, a random copolymer is used.

The molecular weight of the polyoxyalkylene/polyoxyethylene copolymer dialkyl ether represented by formula (I) should be 100 to 10000, preferably 150 to 5000, more preferably 200 to 3000, and even more preferably 300 to 2000. The ratio [EO/(AO+EO)] of the amount of EO to the total amount of AO and EO in each molecule is preferably 20% to 80% by mass.

Specific examples of polyoxyalkylene/polyoxyethylene copolymer dialkyl ethers that can be favorably used in the present invention include, but are not limited to, the following polyoxypropylene/polyoxyethylene copolymer dimethyl ethers:

PEG/PPG-9/2 dimethyl ether
PEG/PPG-17/4 dimethyl ether
PEG/PPG-14/7 dimethyl ether PEG/PPG-11/9 dimethyl ether
PEG/PPG-55/28 dimethyl ether
PEG/PPG-36/41 dimethyl ether
PEG/PPG-6/3 dimethyl ether
PEG/PPG-8/4 dimethyl ether
PEG/PPG-6/11 dimethyl ether
PEG/PPG-14/27 dimethyl ether The polyoxyalkylene/polyoxyethylene copolymer dialkyl ether tends to have better ultraviolet protection performance increase effects due to heat as the molecular weight becomes relatively smaller. Therefore, among the polyoxypropylene/polyoxyethylene copolymer dimethyl ethers listed above, PEG/PPG-9/2 dimethyl ether exhibits the strongest effects.

Meanwhile, examples of the (ii) polyhydric alcohol that can be used in the present invention include the polyalkylene glycols of formula (II) below, as well as butylene glycol, dipropylene glycol, diglycerin, propanediol, erythritol, xylitol, methylglyceth-10, sorbitol and the like.

In this case, the polyalkylene glycols are represented by the following formula (II):

$$HO(RO)_pH \qquad (II)$$

In the above formula, RO denotes an oxyalkylene group having two to four carbon atoms, and p is 3 to 500.

Specifically, it is selected from among those usable in skin preparations for external use, such as cosmetics, and includes polyethylene glycol (also represented by "PEG"), polypropylene glycol (also represented by "PPG") and polybutylene glycol (also represented by "PBG") and the like.

Among the above, polyethylene glycols in which, in formula (II) above, RO is an oxyethylene group, and p is in the range 3 to 500, more preferably 3 to 60, are preferred. The preferred average molecular weight of the polyethylene glycol is within the range 150 to 23000, more preferably 150 to 3000. Specific examples include polyethylene glycol 300, polyethylene glycol 400, polyethylene glycol 1500, polyethylene glycol 20000 and the like.

The polyalkylene glycol tends to have better ultraviolet protection performance increase effects due to heat as the molecular weight becomes relatively smaller. Therefore, among the polyethylene glycols listed above, particularly strong effects are obtained when polyethylene glycol 300 or polyethylene glycol 400 is used.

Component (B) in the present invention includes embodiments consisting only of an alkylene oxide derivative, embodiments consisting only of a polyhydric alcohol, and embodiments including both an alkylene oxide derivative and a polyhydric alcohol.

In particular, in order to maximum the ultraviolet protection performance increase effects, at least one each of an alkylene oxide derivative and a polyhydric alcohol are preferably included. For example, in the case in which a combination of a low-molecular-weight polyoxypropylene/polyoxyethylene copolymer dimethyl ether having an average molecular weight of 150 to 3000 is combined with a polyalkylene glycol having an average molecular weight of 150 to 3000, the ultraviolet protection performance increase effects due to heat become prominent. Specific examples include, in particular, a combination of polyethylene glycol 300 and PEG/PPG-9/2 dimethyl ether, and a combination of polyethylene glycol 400 and PEG/PPG-9/2 dimethyl ether.

The blended amount of component (B) should be at least 1.0% by mass or more, more preferably 2.5% by mass or more, and 20% by mass or less, more preferably 15% by mass or less relative to the total amount of the cosmetic. If the blended amount is less than 1.0% by mass, then there are cases in which ultraviolet protection performance increase effects due to heat cannot be sufficiently obtained. In particular, if the amount is 2.5% by mass or more, then the effects can be more reliably achieved. Additionally, if the amount exceeds 20% by mass, then the stability and the texture may be affected.

<Component (A)/Component (B) Mass Ratio>

In the cosmetic according to the present invention, the blend is preferably such that the component (A)/component (B) mass ratio is 20 or lower, and more preferably 13 or lower. If there is too little of component (B) relative to component (A) (if the mass ratio is too high), then there are cases in which ultraviolet protection performance increase effects due to heat cannot be sufficiently obtained, and conversely, if there is too much of component (B) relative to component (A) (if the mass ratio is too low), then there is a tendency for the texture to become worse.

<(C) Oil Phase Thickener>

The (C) oil phase thickener (hereinafter sometimes referred to simply as "component (C)") blended in the present invention can be appropriately selected from among substances that are used, in normal emulsion cosmetics or the like, as components for achieving the effect of thickening the oil phase by dissolving into oils or being swollen with oils. For example, dextrin fatty acid esters, sucrose fatty acid esters, solid or semi-solid hydrocarbon oils, organically modified clay minerals, fatty acids or salts thereof, and the like are preferred, among which it is particularly preferable to blend two or more types selected from the above.

Dextrin fatty acid esters are esters of dextrin or reduced dextrin with a higher fatty acid, which may be used without any particular restrictions as long as they are generally used in cosmetics. As the dextrin or reduced dextrin, one in which the average degree of sugar polymerization is 3 to 100 is preferably used. Additionally, as the constituent fatty acids in the dextrin fatty acid ester, a saturated fatty acid having 8 to 22 carbon atoms is preferably used. Specific examples include dextrin palmitate, dextrin oleate, dextrin stearate, dextrin myristate, dextrin (palmitate/2-ethylhexanoate) and the like.

As the sucrose fatty acid esters, those in which the fatty acid is linear or branched, saturated or unsaturated, and having 12 to 22 carbon atoms are preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters and the like.

The solid or semi-solid hydrocarbon oils are hydrocarbons that are solid or semi-solid at ambient temperature (25° C.), specific examples of which include vaseline, hydrogenated palm oil, hydrogenated castor oil (castor wax), hardened palm kernel oil, hardened castor oil, hydrogenated peanut oil, hydrogenated rapeseed oil, hydrogenated *camellia* oil, hydrogenated soybean oil, hydrogenated olive oil, hydrogenated macadamia nut oil, hydrogenated sunflower oil, hydrogenated wheat germ oil, hydrogenated rice germ oil, hydrogenated rice bran oil, hydrogenated cottonseed oil, hydrogenated avocado oil, waxes and the like.

The organically modified clay minerals are a type of colloidal hydrated ammonium silicate having a three-layered structure, representative of which is a clay mineral modified by a quaternary ammonium salt-type cationic surfactant, represented by the following general formula (III):

$$(X,Y)_{2-3}(Si,Al)_4O_{10}(OH)_2Z_{1/3} \cdot nH_2O \qquad (III)$$

where X=Al, Fe(III), Mn(III) or Cr(III); Y=Mg, Fe(II), Ni, Zn or Li; and Z=K, Na or Ca.

Specific examples include dimethyl distearyl ammonium hectorite (distearyldimonium hectorite), dimethyl alkyl ammonium hectorite, benzyl dimethyl stearyl ammonium hectorite, distearyl dimethyl ammonium chloride-treated aluminum-magnesium silicate and the like. As commercial products, Bentone 27 (benzyl dimethyl stearyl ammonium chloride-treated hectorite, manufactured by Elementis Japan) and Bentone 38 (distearyl dimethyl ammonium chloride-treated hectorite, manufactured by Elementis Japan) are preferred.

The fatty acid is not particularly limited as long as it can be used in a cosmetic or the like, and may be selected from among fatty acids having linear or branched saturated or unsaturated hydrocarbon groups. In particular, there are higher fatty acids that are solid at ambient temperature and have 8 to 22 carbon atoms such as, for example, lauric acid, myristic acid, palmitic acid, stearic acid, behenic acid, oleic acid, isomyristic acid, isopalmitic acid and the like. Among the above, it is particularly preferable to use one or more types selected from among stearic acid, palmitic acid and behenic acid. As salts of fatty acids, there are metal salts such as sodium salts, calcium salts, magnesium salts and aluminum salts. Additionally, fatty acid amide derivatives or ester derivatives may also be used.

The blended amount of the oil phase thickener (component (C)) in the cosmetic of the present invention should be adjusted so that the moisture content of a coating film, when coming into contact with moisture, is sufficient to allow the oil phase thickener to move within the coating film. Specifically, the blended amount of the oil phase thickener may be 0.1% to 25% by mass, preferably 0.3% to 18% by mass, and more preferably 0.5% to 13% by mass relative to the total amount of the cosmetic.

<Optional Blended Components>

Aside from the above-mentioned components (A) to (C), components that are normally used in cosmetics may be blended into the cosmetic of the present invention within a range not compromising the effects of the present invention. For example, it is possible to appropriately blend, as needed, surfactants, oils, powder components, pH adjusters, chelating agents, preservatives, antioxidants, medicinal agents, alcohols, colorants, pigments and the like. Examples of medicinal agents include ascorbic acid (vitamin C), tranexamic acid, kojic acid, ellagic acid, albutin, alkoxysalicylic acid, nicotinic acid amide, glycyrrhizinic acid, tocopherol, retinol, and salts or derivatives of the above (e.g., sodium L-ascorbate, L-ascorbic acid ester magnesium salts, L-ascorbic acid glucoside, 2-O-ethyl-L-ascorbic acid, 3-O-ethyl-L-ascorbic acid, 4-methoxysalicylic acid sodium salts, 4-methoxysalicylic acid potassium salts, dipotassium glycyrrhizinate, stearyl glycyrrhizinate, tocopherol acetate, retinol acetate, retinol palmitate, etc.). Additionally, humectants having an IOB value higher than 5, such as glycerin, may also be blended within a range not inhibiting the effects of the present invention.

Additionally, as a surfactant, in the case of a water-in-oil emulsion cosmetic, a surfactant having a silicone backbone (polysiloxane structure) and having an HLB lower than 8 is preferred. For example, it is preferable to use a polyoxyalkylene-modified silicone, a polyoxyalkylene/alkyl co-modified silicone, a polyglycerin-modified silicone and/or a polyglycerin/alkyl co-modified silicone, among which a polyoxyalkylene-modified silicone or a polyoxyalkylene/alkyl-modified silicone is more preferred.

Meanwhile, in the case of an oil-in-water emulsion cosmetic, the surfactant may be of one or more types selected from among non-ionic surfactants that are conventionally used in oil-in-water emulsion cosmetics, among which those having an HLB of 6 or higher are preferably used. In particular, one containing polyoxyethylene hardened castor oil is particularly preferred for the purposes of stability of the preparation and light absorption increase effects due to contact with moisture. Specific examples of polyoxyethylene hardened castor oils include PEG-10 hydrogenated castor oil, PEG-20 hydrogenated castor oil, PEG-25 hydrogenated castor oil, PEG-30 hydrogenated castor oil, PEG-40 hydrogenated castor oil, PEG-50 hydrogenated castor oil, PEG-60 hydrogenated castor oil, PEG-80 hydrogenated castor oil, PEG-100 hydrogenated castor oil and the like. If a polyoxyethylene hardened castor oil is not to be included, then a non-ionic surfactant having an HLB of 8 or higher, preferably 10 or higher, and more preferably 12 or higher is preferably used.

Examples of oils include volatile oils and non-volatile oils that are normally used in cosmetics. In particular, in the case of an emulsion cosmetic, it is preferable to blend an ester oil having an IOB value of 0.3 or higher into the oil phase thereof.

Volatile oils include volatile hydrocarbon oils and volatile silicone oils.

The volatile hydrocarbon oils are not particularly limited as long as they are hydrocarbon oils that are volatile at ambient temperature (25° C.) and that are conventionally used in cosmetics and the like. Specific examples include isododecane, isohexadecane, hydrogenated polyisobutene and the like.

The volatile silicone oils are silicone oils that are volatile at ambient temperature (25° C.) and that are conventionally used in cosmetics and the like, including cyclic dimethylpolysiloxanes having four to six silicon atoms and chain dimethylpolysiloxanes having two to five silicon atoms. Specific examples include cyclic silicone oils such as hexamethylcyclotrisiloxane (D3), octamethyltetracyclosiloxane (D4), decamethylcyclopentasiloxane (D5) and dodecamethylcyclohexasiloxane (D6), diphenylsiloxyphenyl trimethicone, volatile dimethicone (as commercially available products, KF-96L-1.5cs and KF-96L-2cs; manufactured by Shin-Etsu Chemical) and the like.

Non-volatile oils include, for example, hydrocarbon oils, vegetable oils, ester oils, high-molecular-weight polyoxyalkylene glycol and silicone oils.

Specific examples include liquid oils and fats such as palm oil, linseed oil, *camellia* oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cottonseed oil, soybean oil, peanut oil, tea seed oil, evening primrose oil, egg yolk oil, liver oil, triglycerin, glyceryl trioctanoate, glyceryl triisopalmitate and the like; ester oils including octanoic acid esters such as cetyl octanoate, isooctanoic acid esters such as glyceryl tri-2-ethylhexanoate and pentaerythrityl tetra-2-ethylhexanoate, lauric acid esters such as hexyl laurate, myristic acid esters such as isopropyl myristate and octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate, and diisostearyl malate; hydrocarbon oils such as liquid paraffin and squalane; and silicone oils such as polyoxybutylene polyoxypropylene glycol and polydimethylsiloxane.

Additionally, as a powder component, it is particularly preferable to blend in approximately 1% to 30% by mass of a spherical resin powder, since this further improves the texture and allows a good, silky touch to be obtained. The spherical resin powder may be arbitrarily used without any particular restrictions, as long as it is of a type that is blended into cosmetic products or the like in general. Examples include (meth)acrylic acid ester resin powders, polyamide resin powders (nylon powders), polyethylene powders, polystyrene powders, styrene/(meth)acrylic acid copolymer resin powders, benzoguanamine resin powders, polytetrafluoroethylene powders, cellulose powders, trimethyl silsesquioxane powders and the like, as well as organopolysiloxane elastomer spherical powders or composite spherical powders having the above as base powders. Although the particle sizes or the like of the blended spherical resin powders are not particularly limited, one in which the particle size is, for example, approximately 1 to 50 μm may be favorably used. Additionally, these spherical resin powders may be subjected to hydrophobic treatments.

An example of a commercially available spherical organic resin powder is Ganzpearl (manufactured by AICA Kogyo), and examples of commercially available spherical silicone resin powders include Trefil E-505C, Trefil E-506C, Trefil E-506S, Trefil HP40T (all manufactured by Toray Dow Corning Silicone), Tospearl 145A (manufactured by Toshiba Silicone), and silicone powders KSP-100 and KSP-300 (manufactured by Shin-Etsu Chemical) and the like.

The cosmetic of the present invention may be in the form of an oil-based cosmetic, a water-in-oil emulsion cosmetic, an oil-in-water emulsion cosmetic, a multi-phase emulsion cosmetic or a water-based cosmetic, and is not particularly limited.

As the product form, the cosmetic may be provided not only as a sunscreen cosmetic, but also as a makeup base or a makeup cosmetic such as a foundation provided with sunscreen effects, a hair cosmetic (including various types of hair-care products such as hairsprays and hair treatments for protecting the hair or scalp from ultraviolet rays), a spray-type cosmetic or the like.

The cosmetic of the present invention has the novel property in which the ultraviolet protection effects of a coating film are increased by coming into contact with moisture and/or by heat.

"The ultraviolet protection effects are increased by coming into contact with moisture and/or by heat" can be defined, in summary, as indicated below.

A prescribed amount of a sample of the cosmetic is dripped onto a measurement plate, coated over a prescribed area and dried to form a coating film. The absorbance of the coating film is measured from 400 to 280 nm by means of a spectrophotometer or the like, and the absorbance integral value of the coating film is determined by using the absorbance of an uncoated measurement plate as a reference.

Next, when investigating the increase in the ultraviolet protection effects due to coming into contact with moisture, a measurement plate on which the coating film has been formed is immersed in water under prescribed conditions and dried, after which the absorbance of the coating film is measured and the absorbance integral value is similarly determined. Meanwhile, when investigating the increase in the ultraviolet protection effects due to heat, a measurement plate on which the coating film has been formed is heated under prescribed conditions, the absorbance of the coating film is measured after returning to ambient temperature, and the absorbance integral value is similarly determined.

The rate of change in the absorbance integral value after a water bath treatment or a heat treatment is calculated in accordance with the following equation.

Absorbance integral value change (%)=(post-treatment absorbance integral value)/(pre-treatment absorbance integral value)×100

If the rate of change in the absorbance integral value exceeds 100%, then the ultraviolet protection effect is defined as having increased. In the cosmetic of the present invention, the rate of change in the absorbance integral value exceeds at least 100%, and is preferably 103% or higher, more preferably 105% or higher, even more preferably 110% or higher, and particularly preferably 115% or higher.

When investigating the increase in the ultraviolet protection effects due to coming into contact with moisture, the measurement plate should preferably be immersed for approximately 20 minutes to 1 hour in water having a hardness of 50 to 500, at ambient temperature. Additionally, the absorbance should preferably be measured after being dried for approximately 10 to 30 minutes after immersion.

When investigating the increase in the ultraviolet protection effects due to heat, the heating temperature should preferably be within the range from 30° C. to 70° C. For example, the temperature may be 32° C. or higher, 35° C. or higher, 37° C. or higher, or 40° C. or higher, and 65° C. or lower, 60° C. or lower, 55° C. or lower, or 50° C. or lower. If the heating temperature exceeds 70° C., then there may be problems such as a resin-composed measurement plate melting or the like.

In order to accurately evaluate the effects of heat, the heating time should preferably be 1 minute or longer, more preferably 10 minutes or longer. The upper limit of the processing time is not particularly limited, but should be 60 minutes or shorter, preferably 30 minutes or shorter.

EXAMPLES

Hereinafter, the present invention will be explained in further detail by providing specific examples. However, the present invention is not limited to the examples below. Additionally, the blended amounts in the following examples and the like are indicated in percentage by mass where not particularly indicated otherwise. Before specifically explaining each example, the evaluation method that was used will be explained.

(1) Post-Water Bath Light Absorbance Integral Value Change

Samples of each example were dripped, in the amount of 2 mg/cm$^2$, onto S plates (5×5 cm V-groove PMMA plate, SPFMASTER-PA01), spread with a finger for 60 seconds, and dried for 15 minutes to form coating films. Using an uncoated plate as a control, the absorbances (400 to 280 nm) of the coating films were measured with a Hitachi U-3500 self-recording spectrophotometer, and the obtained measurement data was used to determine pre-water bath absorbance integral values.

Next, the measured plates were fully immersed in water having a hardness of 50 to 500, and agitated (300 rpm using a 3-1 motor) in the water for 30 minutes. Thereafter, the plates were dried for about 15 to 30 minutes until the water droplets on the surfaces disappeared, the absorbances were measured again, and the post-water bath light absorbance integral values were determined from the resulting measurement data.

The rates of change (%) of the post-water bath absorbance integral values were computed from the following equation.

Post-water bath absorbance integral value change (%)=(post-water bath absorbance integral value)/(pre-water bath absorbance integral value)×100

(2) Post-Heating Absorbance Integral Value Change

Absorbance integral values were determined in the same manner as that described above, except that the water bath was replaced by heat-treating the plates at 37° C. for 30 minutes in a thermostatic chamber, then the rates of change (%) of the post-heating absorbance integral values were computed from the following equation.

Post-heating absorbance integral value change (%)=(post-heating absorbance integral value)/(pre-heating absorbance integral value)×100

Experimental Examples 1 to 21

Water-in-oil emulsion cosmetics having the compositions indicated in Tables 1 to 3 below were prepared in accordance with conventional methods, and the rates of change in the post-water bath and post-heating absorbance integral values were measured in accordance with the abovementioned evaluation methods.

TABLE 1

|  | Exp. Ex. 1 | Exp. Ex. 2 | Exp. Ex. 3 | Exp. Ex. 4 | Exp. Ex. 5 | Exp. Ex. 6 | Exp. Ex. 7 | Exp. Ex. 8 |
|---|---|---|---|---|---|---|---|---|
| Water | bal | bal | bal | bal | bal | bal | bal | bal |
| Ethanol | 10 | 10 | 10 | 10 | 10 | 10 | 10 | 10 |
| PEG/PPG-9/2 dimethyl ether (IOB = 1.5) | — | — | — | 5 | 3 | 1.5 | 1 | 0.6 |
| Distearyldimonium hectorite | — | 0.5 | 0.5 | 0.5 | 0.5 | 0.5 | 0.5 | 0.5 |
| Dextrin fatty acid ester | — | — | 1 | 1 | 3 | 4.5 | 5 | 5.4 |
| PEG-9 polydimethyl siloxyethyl dimethicone | 2 | 2 | 2 | 2 | 2 | 2 | 2 | 2 |
| Diisopropyl sebacate | 10 | 10 | 10 | 10 | 10 | 10 | 10 | 10 |
| Cyclomethicone | 20 | 20 | 20 | 20 | 20 | 20 | 20 | 20 |
| Volatile dimethicone | 10 | 10 | 10 | 10 | 10 | 10 | 10 | 10 |
| Isostearic acid | 1 | 1 | 1 | 1 | 1 | 1 | 1 | 1 |
| Octocrylene | 5 | 5 | 5 | 5 | 5 | 5 | 5 | 5 |
| bis-Ethylhexyloxyphenol methoxyphenyl triazine | 1 | 1 | 1 | 1 | 1 | 1 | 1 | 1 |
| Diethylamino hydroxybenzoyl hexyl benzoate | 1 | 1 | 1 | 1 | 1 | 1 | 1 | 1 |
| Ethylhexyl triazone | 1 | 1 | 1 | 1 | 1 | 1 | 1 | 1 |
| Ethylhexyl methoxy cinnamante | 5 | 5 | 5 | 5 | 5 | 5 | 5 | 5 |
| Hydrophobically treated fine-particle titanium oxide | 4 | 4 | 4 | 4 | 4 | 4 | 4 | 4 |
| Hydrophobically treated fine-particle zinc oxide | 10 | 10 | 10 | 10 | 10 | 10 | 10 | 10 |
| Spherical silicone rubber powder | 3 | 3 | 3 | 3 | 3 | 3 | 3 | 3 |
| Hydrophobically treated talc | 3 | 3 | 3 | 3 | 3 | 3 | 3 | 3 |
| Spherical crosslinked PMMA powder | 3 | 3 | 3 | 3 | 3 | 3 | 3 | 3 |
| Spherical silica | 3 | 3 | 3 | 3 | 3 | 3 | 3 | 3 |
| Chelating agent | s.a. | s.a | s.a. | s.a. | s.a. | s.a. | s.a. | s.a. |
| Total | 100 | 100 | 100 | 100 | 100 | 100 | 100 | 100 |
| Post-water bath absorbance integral value change (%) | 25% | 89% | 102% | 106% | 110% | 117% | 124% | 126% |
| Post-heating absorbance integral value change (%) | 45% | 100% | 97% | 124% | 110% | 107% | 106% | 97% |
| (A) Ultraviolet protectant/(B) humectant mass ratio | — | — | — | 2.6 | 4.3 | 8.7 | 13.0 | 21.7 |

As shown in Table 1, when a humectant was not blended, there were no cases in which the rate of change in the post-heating absorbance integral value exceeded 100% (Experimental Examples 1 to 3). Meanwhile, it was observed that, by blending a humectant, the rate of change in the post-heating absorbance integral values exceeds 100%, and the ultraviolet protection effects are increased by heat (Experimental Examples 4 to 7). However, an increase in the ultraviolet protection effects due to heat was not observed when the blended amount of the humectant was too small (Experimental Example 8). Additionally, it was observed that an increase in the ultraviolet protection effects due to coming into contact with water was not obtained when an oil phase thickener was not blended or when the blended amount thereof was too small (Experimental Examples 1 and 2), but that an increase was obtained by blending a sufficient amount of an oil phase thickener (Experimental Examples 3 to 8).

TABLE 2

| | Exp. Ex. 9 | Exp. Ex. 10 | Exp. Ex. 11 | Exp. Ex. 12 | Exp. Ex. 13 | Exp. Ex. 14 | Exp. Ex. 15 |
|---|---|---|---|---|---|---|---|
| Water | bal | bal | bal | bal | bal | bal | bal |
| Ethanol | 10 | 10 | 10 | 10 | 10 | 10 | 10 |
| PEG/PPG-9/2 dimethyl ether (IOB = 1.5) | 3 | 3 | — | — | — | — | — |
| PEG/PPG-14/7 dimethyl ether (IOB = 1.3) | — | — | 3 | — | — | — | — |
| Polyethylene glycol 300 (IOB = 2.3) | 3 | — | — | 3 | — | — | — |
| Polyethylene glycol 1500 (IOB = 2) | — | — | — | — | 3 | — | — |
| Polyethylene glycol 20000 (IOB = 1.9) | — | — | — | — | — | 3 | — |
| Glycerin (IOB = 6) | — | — | — | — | — | — | 3 |
| Distearyldimonium hectorite | 0.5 | 0.5 | 0.5 | 0.5 | 0.5 | 0.5 | 0.5 |
| Dextrin fatty acid ester | 1 | 1 | 1 | 1 | 1 | 1 | 1 |
| PEG-9 polydimethyl siloxyethyl dimethicone | 2 | 2 | 2 | 2 | 2 | 2 | 2 |
| Diisopropyl sebacate | 10 | 10 | 10 | 10 | 10 | 10 | 10 |
| Cyclomethicone | 20 | 20 | 20 | 20 | 20 | 20 | 20 |
| Volatile dimethicone | 10 | 10 | 10 | 10 | 10 | 10 | 10 |
| Isostearic acid | 1 | 1 | 1 | 1 | 1 | 1 | 1 |
| Octocrylene | 5 | 5 | 5 | 5 | 5 | 5 | 5 |
| bis-Ethylhexyloxyphenol methoxyphenyl triazine | 1 | 1 | 1 | 1 | 1 | 1 | 1 |
| Diethylamino hydroxybenzoyl hexyl benzoate | 1 | 1 | 1 | 1 | 1 | 1 | 1 |
| Ethylhexyl triazone | 1 | 1 | 1 | 1 | 1 | 1 | 1 |
| Ethylhexyl methoxy cinnamante | 5 | 5 | 5 | 5 | 5 | 5 | 5 |
| Hydrophobically treated fine-particle titanium oxide | 4 | 4 | 4 | 4 | 4 | 4 | 4 |
| Hydrophobically treated fine-particle zinc oxide | 10 | 10 | 10 | 10 | 10 | 10 | 10 |
| Spherical silicone rubber powder | 3 | 3 | 3 | 3 | 3 | 3 | 3 |
| Hydrophobically treated talc | 3 | 3 | 3 | 3 | 3 | 3 | 3 |
| Spherical crosslinked PMMA powder | 3 | 3 | 3 | 3 | 3 | 3 | 3 |
| Spherical silica | 3 | 3 | 3 | 3 | 3 | 3 | 3 |
| Chelating agent | s.a. | s.a | s.a. | s.a. | s.a. | s.a. | s.a. |
| Total | 100 | 100 | 100 | 100 | 100 | 100 | 100 |
| Post-water bath absorbance integral value change (%) | 105% | 106% | 108% | 105% | 106% | 106% | 106% |
| Post-heating absorbance integral value change (%) | 129% | 120% | 117% | 113% | 110% | 105% | 100% |
| (A) Ultraviolet protectant/(B) humectant mass ratio | 2.2 | 4.3 | 4.3 | 4.3 | 4.3 | 4.3 | 4.3 |

As shown in Table 2, it was observed that, by blending a humectant, particularly one having an IOB of 3 or lower, the ultraviolet protection effects due to heat were increased (Experimental Examples 9 to 14). However, said effects could not be observed when glycerin, which has an IOB that is too high, was used as the humectant (Experimental Example 15). Additionally, for both alkylene oxide derivatives and polyhydric alcohol derivatives, a tendency for the ultraviolet protection effects due to heat to increase greatly as the molecular weights became smaller was observed. In fact, when containing PEG/PPG-9/2 dimethyl ether and polyethylene glycol 300 as humectants, the ultraviolet protection effects due to heat increased significantly (Experimental Example 9).

TABLE 3

|  | Exp. Ex. 16 | Exp. Ex. 17 | Exp. Ex. 18 | Exp. Ex. 19 | Exp. Ex. 20 | Exp. Ex. 21 |
| --- | --- | --- | --- | --- | --- | --- |
| Water | bal | bal | bal | bal | bal | bal |
| Ethanol | 10 | 10 | 10 | 10 | 10 | 10 |
| PEG/PPG-9/2 dimethyl ether (IOB = 1.5) | 3 | 3 | 3 | 3 | 3 | 3 |
| Distearyldimonium hectorite | 0.5 | 0.5 | 0.5 | 0.5 | 0.5 | 0.5 |
| Sucrose fatty acid ester | 2 | — | — | — | — | — |
| Polyamide-8 | — | 2 | — | — | — | — |
| Dibutyl lauroyl glutamide | — | — | 1 | — | — | — |
| Hydroxystearic acid | — | — | — | 2 | — | — |
| Castor oil/isophorone diisocyanate copolymer | — | — | — | — | 2 | — |
| Glycerin fatty acid ester | — | — | — | — | — | 2 |
| PEG-9 polydimethyl siloxyethyl dimethicone | 2 | 2 | 2 | 2 | 2 | 2 |
| Diisopropyl sebacate | 10 | 10 | 10 | 10 | 10 | 10 |
| Cyclomethicone | 20 | 20 | 20 | 20 | 20 | 20 |
| Volatile dimethicone | 10 | 10 | 10 | 10 | 10 | 10 |
| Isostearic acid | 1 | 1 | 1 | 1 | 1 | 1 |
| Octocrylene | 5 | 5 | 5 | 5 | 5 | 5 |
| bis-Ethylhexyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Ethylhexyl triazone | 1 | 1 | 1 | 1 | 1 | 1 |
| Ethylhexyl methoxycinnamante | 5 | 5 | 5 | 5 | 5 | 5 |
| Hydrophobically treated fine-particle titanium oxide | 4 | 4 | 4 | 4 | 4 | 4 |
| Hydrophobically treated fine-particle zinc oxide | 10 | 10 | 10 | 10 | 10 | 10 |
| Spherical silicone rubber powder | 3 | 3 | 3 | 3 | 3 | 3 |
| Hydrophobically treated talc | 3 | 3 | 3 | 3 | 3 | 3 |
| Spherical crosslinked PMMA powder | 3 | 3 | 3 | 3 | 3 | 3 |
| Spherical silica | 3 | 3 | 3 | 3 | 3 | 3 |
| Chelating agent | s.a. | s.a | s.a. | s.a. | s.a. | s.a. |
| Total | 100 | 100 | 100 | 100 | 100 | 100 |
| Post-water bath absorbance integral value change (%) | 105% | 114% | 116% | 119% | 105% | 110% |
| Post-heating absorbance integral value change (%) | 113% | 116% | 119% | 113% | 116% | 117% |
| (A) Ultraviolet protectant/(B) humectant mass ratio | 4.3 | 4.3 | 4.3 | 4.3 | 4.3 | 4.3 |

As indicated in Table 3, it was observed that, if a sufficient amount of a humnectant is included, then the ultraviolet protection effects due to coming into contact with moisture and heating increase even when the type of oil phase thickener is changed (Experimental Examples 16 to 21).

Experimental Example 22

An oil-in-water emulsion cosmetic having the composition shown in Table 4 below was prepared in accordance with a conventional method, and the rates of change in the post-water bath and the post-heating absorbance integral values were measured in accordance with the evaluation method described above.

TABLE 4

|  | Exp. Ex. 22 |
| --- | --- |
| Water | bal |
| Glycerin | 4 |
| 1,3-Butylene glycol | 7 |
| PEG/PPG-9/2 dimethyl ether | 5 |
| Succinoglycan | 0.3 |
| Sucrose fatty acid ester | 3 |
| (Dimethylacrylamide/sodium acryloyldimethyl taurate) cross-polymer | 0.3 |
| PEG-60 hydrogenated castor oil | 2 |
| Diisopropyl sebacate | 2 |
| Non-volatile dimethicone | 2 |
| Cyclomethicone | 12 |
| Triethyl hexanoin | 5 |
| Isostearic acid | 1 |
| Sorbitan sequiisostearate | 0.5 |
| Hydrophobically treated fine-particle zinc oxide | 10 |
| Ethylhexyl methoxycinnamante | 10 |
| Diethylamino hydroxybenzoyl hexyl benzoate | 1 |
| bis-Ethylhexyloxyphenol methoxyphenyl triazine | 1 |
| Spherical urethane resin powder | 3 |
| Citric acid | s.a. |

TABLE 4-continued

| | Exp. Ex. 22 |
|---|---|
| Sodium citrate | s.a. |
| Chelating agent | s.a. |
| Preservative | s.a. |
| Total | 100 |
| Post-water bath absorbance integral value change (%) | 107% |
| Post-heating absorbance integral value change (%) | 106% |
| (A) Ultraviolet protectant/(B) humectant mass ratio | 0.75 |

As shown in Table 4, it was observed that, even in a cosmetic in oil-in-water emulsion form, the ultraviolet protection effects are increased by coming into contact with moisture and by heating, due to the blending of a prescribed humectant and an oil phase thickener (Experimental Example 22).

Hereinafter, examples of formulations of the cosmetic of the present invention will be indicated. Needless to say, the present invention is not limited in any way by these formulation examples, and is as defined by the claims. The blended amounts are all indicated in percentage by mass relative to the total amount of the cosmetic.

Formulation Example 1: Two-Layer Makeup Base

| (Component name) | Blended amount (% by mass) |
|---|---|
| Purified water | balance |
| Ethanol | 5 |
| PEG/PPG-9/2 dimethyl ether | 4 |
| Glycerin | 1 |
| Xylitol | 1 |
| *Potentilla erecta* extract | 0.3 |
| Sodium hyaluronate | 0.1 |
| 2-O-ethyl-L-ascorbic acid | 0.1 |
| Dipotassium glycyrrhizinate | 0.05 |
| Isododecane | 3 |
| Diisopropyl sebacate | 10 |
| PBG/PPG-9/1 copolymer | 1 |
| Polyethylene glycol 300 | 1 |
| Dimethicone | 10 |
| Caprylyl methicone | 3 |
| Trifluoroalkyl dimethyl trimethyl siloxysilicic acid 50% dimethicone solution | 3 |
| Dextrin palmitate | 2 |
| Ethylhexyl methoxycinnamate | 7 |
| Octocrylene | 3 |
| Diethylamino hydroxybenzoyl hexyl benzoate | 1 |
| bis-Ethylhexyloxyphenol methoxyphenyl triazine | 0.5 |
| Hydrophobic fine-particle titanium oxide | 2 |
| Hydrophobically treated fine-particle zinc oxide | 5 |
| Hydrophobically treated pigment-grade titanium oxide | 1 |
| Hydrophobically treated iron oxide | 0.07 |
| Methyl methacrylate cross-polymer | 2 |
| (Vinyl dimethicone/methicone silsesquioxane) cross-polymer | 2 |
| Hydrophobically treated talc | 4 |
| PEG-9 polydimethyl polysiloyethyl dimethicone | 1.5 |
| PEG/PPG-19/19 dimethicone | 0.3 |
| Dimethyl distearyl ammonium hectorite | 0.4 |
| Isostearic acid | 0.3 |
| Stearic acid | 0.5 |
| EDTA•3Na | s.a. |
| Table salt | s.a. |
| Sodium pyrosulfite | s.a. |
| Tocopherol | s.a. |
| Fragrance | s.a. |

Formulation Example 2: Cream-Type Foundation Cream

| (Component name) | Blended amount (% by mass) |
|---|---|
| Purified water | balance |
| Ethanol | 5 |
| Phenoxyethanol | 1 |
| PEG/PPG-9/2 dimethyl ether | 4 |
| Polyethylene glycol 300 | 1 |
| Glycerin | 3 |
| Erythritol | 1 |
| Xylitol | 1 |
| *Potentilla erecta* extract | 1 |
| Glycylglycine | 0.1 |
| Tranexamic acid | 0.5 |
| Dipotassium glycyrrhizinate | 0.05 |
| Tripropylene glycol pivalate | 2 |
| Diisopropyl sebacate | 5 |
| Dimethicone | 10 |
| Cyclomethicone | 3 |
| Trisiloxysilicic acid 50% cyclopentasiloxane solution | 2 |
| Dextrin palmitate | 2.5 |
| Ethylhexyl methoxycinnamate | 7 |
| Hydrophobic fine-particle titanium oxide | 1 |
| Hydrophobic fine-particle zinc oxide | 7 |
| Hydrophobically treated pigment-grade titanium oxide | 4 |
| Hydrophobically treated iron oxide | 3.2 |
| Hydrophobically treated barium sulfate-coated titanated mica | 0.01 |
| Hydrophobically treated titanated mica | 0.01 |
| Dimethicone cross-polymer 13% cyclopentasiloxane mixture | 2 |
| Polymethyl silsesquioxane | 2 |
| Methyl methacrylate cross-polymer | 2 |
| Hydrophobic fine-particle silica | 0.5 |
| Lauryl PEG-9 polydimethyl polysiloxyethyl dimethicone | 2 |
| (Dimethicone/(PEG-10/15)) cross-polymer | 1 |
| Dimethyl distearyl ammonium hectorite | 1 |
| Isostearic acid | 0.2 |
| Stearic acid | 0.5 |
| Tocopherol | s.a. |
| EDTA•3Na | s.a. |
| Table salt | s.a. |
| Sodium pyrosulfite | s.a. |
| Fragrance | s.a. |

Formulation Example 3: Aerosol Spray-Type Sunscreen

| (Component name) | Blended amount (% by mass) |
|---|---|
| Purified water | balance |
| Ethanol | 5 |
| Polyethylene glycol 300 | 2 |
| Silica | 0.1 |
| Glycerin | 1 |
| PEG/PPG-14/7 dimethyl ether | 3 |
| DL-α-tocopherol acetate | 0.5 |
| D-glutamic acid | 0.1 |
| Stearyl glycyrrhizinate | 0.1 |
| Isododecane | 10 |
| Glyceryl tri-2-ethylhexanoate | 5 |
| Isopropyl myristate | 3 |
| Diisopropyl sebacate | 5 |
| PBG/PPG-9/1 copolymer | 1 |
| Dimethicone | 13 |
| Trisiloxysilicic acid 50% cyclopentasiloxane solution | 0.5 |
| Sucrose tetrastearate triacetate | 0.5 |
| Dextrin palmitate | 2 |
| Ethylhexyl methoxycinnamate | 5 |

| (Component name) | Blended amount (% by mass) |
| --- | --- |
| Diethylamino hydroxybenzoyl hexyl benzoate | 2 |
| bis-Ethylhexyloxyphenol methoxyphenyl triazine | 1 |
| Polysilicone-15 | 2 |
| Octocrylene | 5 |
| Methyl methacrylate cross-polymer | 5 |
| (Vinyl dimethicone/methicone silsesquioxane) cross-polymer | 3 |
| Hydrophobically treated talc | 1 |
| Cetyl PEG/PPG-10/1 dimethicone | 1 |
| Lauryl PEG-9 polydimethyl polysiloxyethyl dimethicone | 1 |
| Dimethyl distearyl ammonium hectorite | 0.5 |
| Isostearic acid | 0.3 |
| Stearic acid | 0.5 |
| Sorbitan sequiisostearate | 0.3 |
| EDTA•3Na | s.a. |
| Tocopherol | s.a. |
| Fragrance | s.a. |

The above-mentioned components were mixed to form a stock solution, and a spray can was filled with the stock solution and LPG at a ratio of 50:50 to obtain an aerosol spray-type sunscreen.

Formulation Example 4: Gel-Type Sunscreen

| (Component name) | Blended amount (% by mass) |
| --- | --- |
| Purified water | balance |
| Ethanol | 8 |
| PEG/PPG-9/2 dimethyl ether | 4 |
| *Rosa roxburghii* extract | 0.1 |
| Stearoxyhydroxypropylmethylcellulose | 0.2 |
| (Dimethylacrylamide/sodium acryloyldimethyl taurate) copolymer | 0.2 |
| Succinoglucan | 0.1 |
| Glycerin | 3 |
| Polyethylene glycol 300 | 1 |
| bis-PEG-18 methyl ether dimethyl silane | 3 |
| PEG/PPG-14/7 dimethyl ether | 1 |
| Polyoxyethylene hardened castor oil (60 mol) | 0.2 |
| Ethylhexyl methoxycinnamate | 10 |

| (Component name) | Blended amount (% by mass) |
| --- | --- |
| Diisopropyl sebacate | 5 |
| Diethylamino hydroxybenzoyl hexyl benzoate | 1 |
| bis-Ethylhexyloxyphenol methoxyphenyl triazine | 3 |
| Hydrophobic fine-particle titanium oxide | 3 |
| Hydrophobically treated fine-particle zinc oxide | 5 |
| Isopropyl myristate | 2 |
| Dextrin palmitate | 0.5 |
| Sucrose stearate acetate | 1 |
| Polypropylene glycol (17) | 1 |
| Di(cholesteryl/phytosteryl) N-lauroyl-L-glutamate | 0.1 |
| Dextrin (palmitate/ethylhexanoate) | 0.5 |
| Fragrance | s.a. |
| Silica | 0.3 |

The invention claimed is:

1. A cosmetic containing
(A) an ultraviolet protectant;
(B) at least one compound that is selected from among (i) polyoxyalkylene/polyoxyethylene copolymer dialkyl ethers represented by the following formula (I):

$$R_1O-[(AO)_m(EO)_n]-R_2 \qquad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, and $m+n \leq 20$; and (ii) polyethylene glycols having an average molecular weight of 150 to 3000; and
(C) an oil phase thickener;
wherein
the mass ratio of component (A)/component (B) is 20 or lower.

2. The cosmetic as in claim 1, wherein component (B) contains at least one each of the (i) polyoxyalkylene/polyoxyethylene copolymer dialkyl ethers and the (ii) polyethylene glycols.

3. The cosmetic as in claim 1, wherein the (C) oil phase thickener is selected from among dextrin fatty acid esters, sucrose fatty acid esters, solid or semi-solid hydrocarbon oils, organically modified clay minerals, or fatty acids or salts thereof.

* * * * *